United States Patent
Blodgett et al.

(10) Patent No.: US 10,667,692 B2
(45) Date of Patent: Jun. 2, 2020

(54) COHERENT OPTICAL IMAGING FOR DETECTING NEURAL SIGNATURES AND MEDICAL IMAGING APPLICATIONS USING COMMON-PATH COHERENT OPTICAL TECHNIQUES

(71) Applicant: The Johns Hopkins University, Baltimore, MD (US)

(72) Inventors: David W. Blodgett, Ellicott City, MD (US); Mark A. Chevillet, Silver Spring, MD (US); Scott M. Hendrickson, Baltimore, MD (US); Michael P. McLoughlin, Sykesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 619 days.

(21) Appl. No.: 15/348,604

(22) Filed: Nov. 10, 2016

(65) Prior Publication Data

US 2017/0135581 A1    May 18, 2017

Related U.S. Application Data

(60) Provisional application No. 62/254,315, filed on Nov. 12, 2015.

(51) Int. Cl.
*A61B 5/00* (2006.01)
*G01B 9/02* (2006.01)
(Continued)

(52) U.S. Cl.
CPC .......... *A61B 5/0066* (2013.01); *A61B 5/0042* (2013.01); *A61B 5/0073* (2013.01);
(Continued)

(58) Field of Classification Search
CPC ......... G03H 1/0443; G03H 2001/0033; G03H 2001/0452; G01B 9/02015;
(Continued)

(56) References Cited

U.S. PATENT DOCUMENTS

| | | | | |
|---|---|---|---|---|
| 4,558,952 A | * | 12/1985 | Kulesh | G01J 9/04 356/486 |
| 2001/0000978 A1 | * | 5/2001 | Hitzenberger | A61B 3/102 356/484 |

(Continued)

*Primary Examiner* — Hwa Andrew Lee
(74) *Attorney, Agent, or Firm* — Sung T. Kim

(57) ABSTRACT

Example apparatuses and methods relating to imaging systems are provided. An example imaging system may include an optical source configured to generate an optical beam, a beam splitter configured to split the optical beam into a reference beam and an object beam, and a beam combiner configured to route a combined beam with reference beam and object beam components along a common path into a target medium. In this regard, the target medium may act upon the combined beam to form a common path interference beam. The example imaging system may further include an imaging sensor configured to receive the common path interference beam and generate common path interference beam data associated with the common path interference beam, and an image data processor configured to analyze the common path interference beam data to generate image data describing the target medium.

19 Claims, 10 Drawing Sheets

(51) Int. Cl.
*G03H 1/00* (2006.01)
*G03H 1/04* (2006.01)
*G03H 1/26* (2006.01)
*G02B 27/10* (2006.01)
*G02B 5/30* (2006.01)
*G02F 2/00* (2006.01)

(52) U.S. Cl.
CPC .......... *A61B 5/0082* (2013.01); *A61B 5/4064* (2013.01); *G01B 9/0203* (2013.01); *G01B 9/02011* (2013.01); *G01B 9/02091* (2013.01); *G03H 1/0005* (2013.01); *G03H 1/0402* (2013.01); *G03H 1/0443* (2013.01); *G03H 1/0465* (2013.01); *G03H 1/265* (2013.01); *A61B 2576/026* (2013.01); *G02B 5/3025* (2013.01); *G02B 27/10* (2013.01); *G02F 2/00* (2013.01); *G03H 2001/0033* (2013.01); *G03H 2001/0436* (2013.01); *G03H 2001/0452* (2013.01); *G03H 2001/0469* (2013.01); *G03H 2222/20* (2013.01); *G03H 2226/02* (2013.01); *G03H 2226/13* (2013.01)

(58) Field of Classification Search
CPC ............ G01B 9/02024; G01B 9/02057; G01B 9/02097; G01J 2009/0223; G01M 11/331
See application file for complete search history.

(56) References Cited

U.S. PATENT DOCUMENTS

| | | | |
|---|---|---|---|
| 2006/0238771 A1* | 10/2006 | Drabarek | G01B 9/02057 356/479 |
| 2008/0049229 A1* | 2/2008 | Feldchtein | G01N 21/4795 356/479 |
| 2017/0131320 A1* | 5/2017 | Blodgett | G01P 3/36 |

* cited by examiner

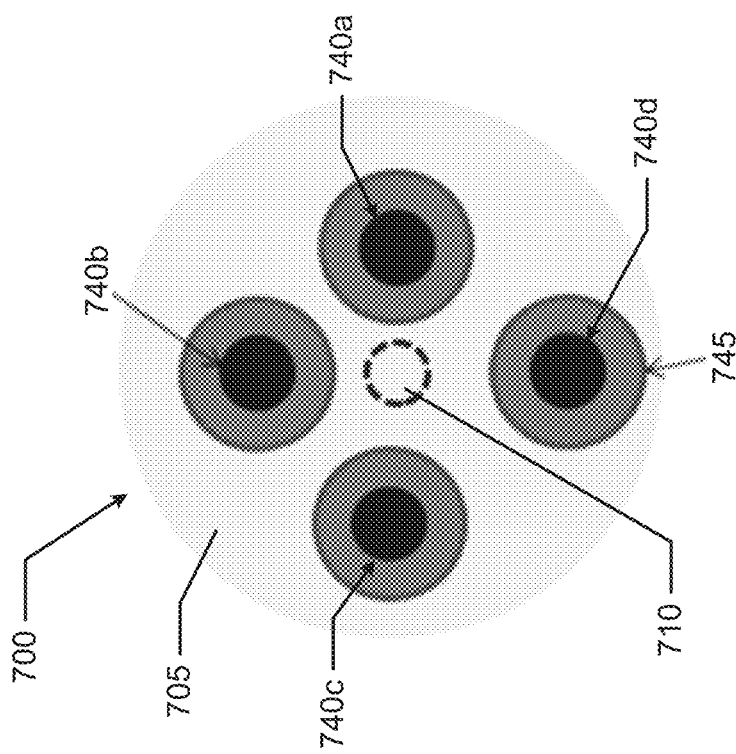
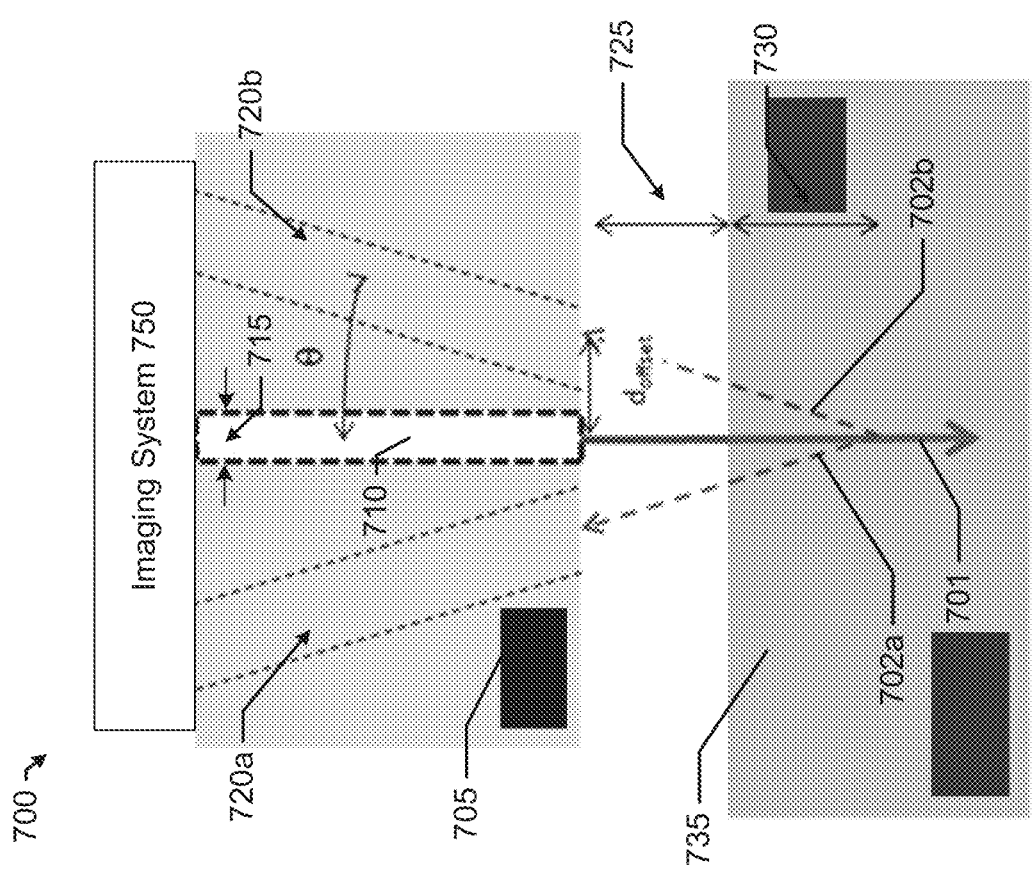

COHERENT OPTICAL IMAGING FOR DETECTING NEURAL SIGNATURES AND MEDICAL IMAGING APPLICATIONS USING COMMON-PATH COHERENT OPTICAL TECHNIQUES

CROSS-REFERENCE TO RELATED APPLICATIONS

This application claims the benefit of U.S. Provisional Application No. 62/254,315 filed on Nov. 12, 2015, the entire contents of which are hereby incorporated herein by reference.

TECHNICAL FIELD

Exemplary embodiments of the present disclosure generally relate to optical imaging techniques, and more specifically relate to employment of coherent optical imaging in any context, including the detection of neural signatures and other medical imaging applications.

BACKGROUND

Coherent optical imaging techniques that analyze the interaction of waves (e.g., light waves) using principles of interferometry can provide a means of achieving near diffraction-limited performance in highly scattering and turbulent environments. These techniques can employ mixing techniques that provide a means for separating object photons, which may be in the form of ballistic or quasi-ballistic photons, from noise or diffuse photons. Diffuse photons do not meet phase (i.e., angle) requirements for coherent mixing conditions between object and reference beams used in a coherent optical imaging approach. Use of a conventional local-oscillator leverages only ballistic photons due to the stringent phase matching conditions that may be employed in optical coherence tomography. According to these conventional techniques, the received object photons must be within some small angular offset of the fixed reference beam. Having such a small angular offset is very restrictive and therefore significantly limits the number of object photons that qualify for use in the imaging analysis. Therefore, it would be advantageous to be able to increase the number of object photons that satisfy the angular requirements to improve imaging quality.

BRIEF SUMMARY OF SOME EXAMPLES

Example apparatuses and methods relating to imaging are provided. According to one example embodiment, an example imaging system is provided. The example imaging system may comprise an optical source configured to generate an optical beam, and a beam splitter configured to split the optical beam into a reference beam and an object beam. The example imaging system may further comprise a beam combiner positioned to receive the reference beam and the object beam, combine the reference beam and the object beam to form a combined beam, and route the combined beam having a reference beam component and an object beam component directed along a common path into a target medium. In this regard, the target medium may act upon the combined beam to form a common path interference beam. The example imaging system may further comprise an imaging sensor configured to receive the common path interference beam and generate common path interference beam data associated with the common path interference beam, and an image data processor configured to analyze the common path interference beam data to generate image data describing the target medium.

According to another example embodiment, an example method is provided. The example method may comprise generating an optical beam by an optical source, splitting the optical beam into a reference beam and an object beam, and routing the reference beam and the object beam along a common path into a target medium. In this regard, the target medium may act upon the reference beam and the object beam to form a common path interference beam. The example method may further comprise receiving the common path interference beam at an imaging sensor, generating common path interference beam data associated with the common path interference beam, and analyzing the common path interference beam data, by an image data processor, to generate image data describing the target medium.

According to another example embodiment, an apparatus comprising a mount is provided. The mount may comprise a transmit slot and a receiver slot. Further, the apparatus may comprise an optical source configured to generate an optical beam, a beam splitter configured to split the optical beam into a reference beam and an object beam, and a beam combiner positioned to receive the reference beam and the object beam, combine the reference beam and the reference beam to form a combined beam, and route the combined beam having a reference beam component and an object beam component directed along a common path via the transmit slot into a target medium. In this regard, the target medium may act upon the combined beam to form a common path interference beam. The apparatus may further comprise an imaging sensor configured to receive the common path interference beam via the receiver slot and generate common path interference beam data associated with the common path interference beam. Additionally, the apparatus may comprise an image data processor configured to analyze the common path interference beam data to generate image data describing the target medium.

BRIEF DESCRIPTION OF THE SEVERAL VIEWS OF THE DRAWING(S)

Having thus described some embodiments of the invention in general terms, reference will now be made to the accompanying drawings, which are not necessarily drawn to scale, and wherein:

FIGS. 7a and 7b illustrate example optical hardware for fixed depth measurements according to various example embodiments;

DETAILED DESCRIPTION

Figure 1:
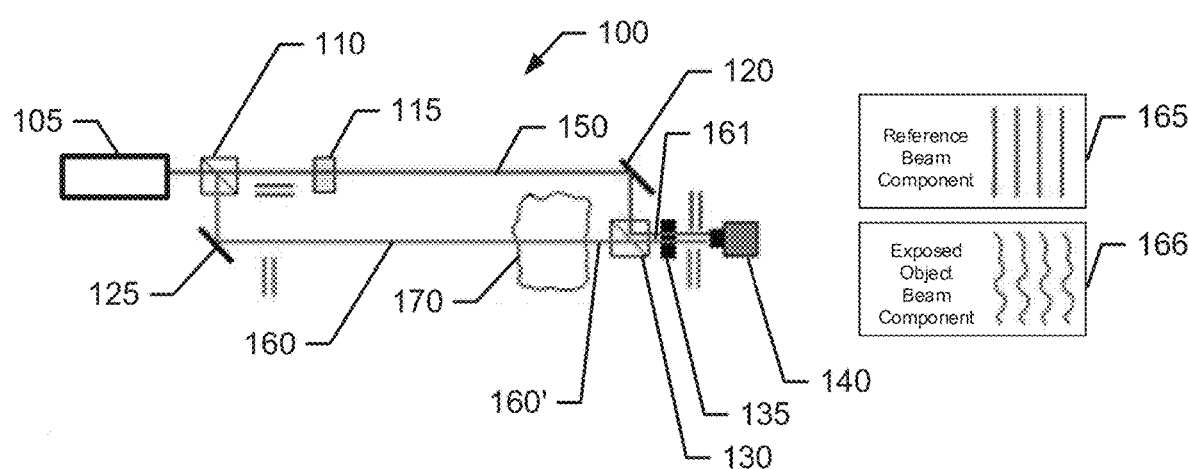
FIG. 1 illustrates a conceptual structure of an optical hardware configuration of an imaging system.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

As used herein, the terms "component," "module," and the like are intended to include a computer-related entity, such as but not limited to hardware, software, firmware, or a combination thereof. For example, a component or module may be, but is not limited to being, a process running on a processor, a processor, an object, an executable, a thread of execution, and/or a computer. By way of example, both an application running on a computing device and/or the computing device can be a component or module. One or more components or modules can reside within a process and/or thread of execution and a component/module may be localized on one computer and/or distributed between two or more computers. In addition, these components can execute from various computer readable media having various data structures stored thereon. The components may communicate by way of local and/or remote processes such as in accordance with a signal having one or more data packets, such as data from one component/module interacting with another component/module in a local system, distributed system, and/or across a network such as the Internet with other systems by way of the signal. Each respective component/module may perform one or more functions that will be described in greater detail herein. However, it should be appreciated that although this example is described in terms of separate modules corresponding to various functions performed, some examples need not necessarily utilize modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, or can be operably coupled to, the processing circuitry to modify the behavior and/or capability of the processing circuitry based on the hardware and/or software that is added to or otherwise operably coupled to the processing circuitry to configure the processing circuitry accordingly.

With reference to imaging systems, as indicated above, having the ability to increase the number of object beam photons that meet the angular requirements for coherent optical imaging techniques would be advantageous because consideration of additional photons results in, for example, improved image quality. According to various example embodiments provided herein, a common path technique is described where the reference beam and the object beam are both exposed to the object or medium to be imaged. More particularly, in contrast to techniques where the reference beam is not exposed to the object, according to various example embodiments, the reference beam can be routed to the object via the same path as the object beam. As a result, the relative phase error between the reference beam and the object beam is reduced and relatively more photons that may be used for imaging analyses will meet the angular requirements for coherent optical imaging.

FIG. 1 provides a conceptual structure of an optical hardware configuration 100 of an imaging system that is in accordance with a conventional coherent optical tomography technique employing a local oscillator. The optical hardware configuration 100 includes an optical source 105 (e.g., a laser or other coherent light source), a beam splitter 110, a frequency shifter 115, mirrors 120 and 125, a beam combiner 130, a polarizer 135 and an imaging sensor 140. The optical hardware configuration 100 may be employed to capture photons at the imaging sensor 140 that generates related data to form an image of the target medium 170. The target medium 170 may be a turbid medium or simply an object such as, for example, neural tissue or other biological matter of a human being, animal, or other organism.

In this regard, the optical source 105 may generate an optical beam that is directed to the beam splitter 110. Beam splitter 110 may split the beam into a reference beam 150 and an object beam 160. Additionally, the beam splitter 110 may generate the reference beam 150 and the object beam 160 such that the beams have relative orthogonal polarizations. The reference beam 150 may also be frequency shifted ($\Delta\omega$) by the frequency shifter 115. After interacting with, or reflecting off, the mirror 125, the object beam 160 may be exposed to the target medium 170 and pass through, at least a portion of the target medium 170. Some photons of the object beam 160 may pass through the target medium 170 and some may be reflected by the target medium 170. According to some example embodiments, the photons that pass completely through the target medium 170 may be utilized for further analysis. Alternatively, or additionally, according to some example embodiments, the photons of the object beam 160 that are reflected by the target medium 170 may be utilized for further analysis. Whether the pass through or the reflected photons are utilized may depend on the particular application and implementation (e.g., hardware implementation), and the photons leaving the target medium 170 after having been exposed to the object beam 160 may be referred to as the exposed beam 160'. Regardless of whether pass through or reflected photons of the object beam 160 are utilized for further analysis, according to some example embodiments, the reference beam 150 is not exposed to the target medium 170. After interacting with the mirror 120, the reference beam 150 may be recombined with the exposed object beam 160' by beam combiner 130. The beam combiner 130 combines the reference beam 150 and the exposed object beam 160' to form a resultant beam 161. The resultant beam 161 leaving the beam combiner 130 includes characteristics that are the result of interference between the reference beam 150 and the exposed object beam 160'. The resultant beam 161 can then be polarized by the polarizer 135 so that the components of the resultant beam 161 (i.e., the reference beam 150 and the exposed object beam 160') have a common polarization. The resultant beam 161 may be received at the imaging sensor 140 for analysis. As can be seen in FIG. 1, the relative phase error between the reference beam component and the exposed object beam component of the resultant beam 161 can be large. An illustration of the relative phase error is provided in FIGS. 1 at 165 and 166, where 165 shows a representation of the reference beam component relative to a representation of the exposed object beam component at 166. In this regard, the exposed object beam 160' may be subjected to scattering and refractive index variations in the target medium 170, while the reference beam 150 is unaffected by the target medium 170 because it is not exposed to the target medium 170. In this configuration, only ballistic photons (i.e., photons that travel through a scattering medium in a straight line) from the object beam 160 can interfere with the reference beam 150.

Figure 2A:
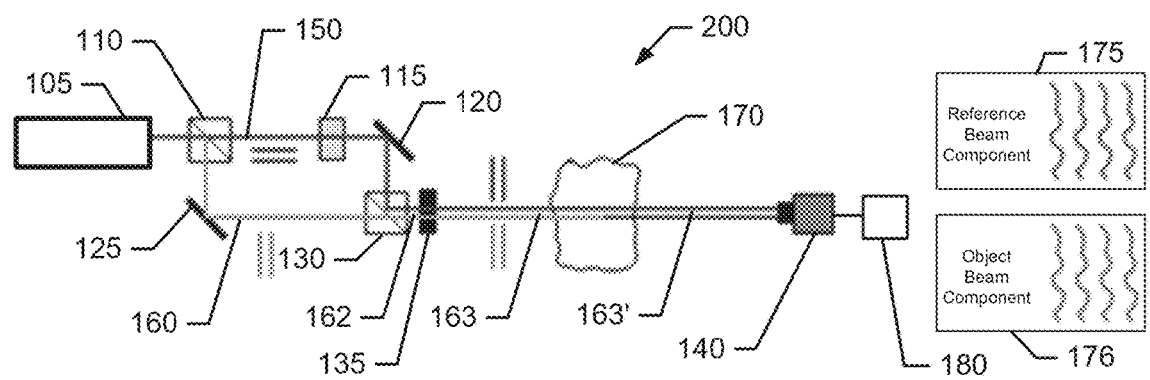
FIG. 2a illustrates a conceptual structure of an imaging system implementing a common path, common polarization approach according to some example embodiments.

Referring now to the implementation of a common-path approach that utilizes a common polarization technique in accordance with various example embodiments, FIG. 2a illustrates a conceptual structure of an imaging system 200 where both the object beam 160 and the reference beam 150 are exposed to the target medium 170. In this regard, according to example embodiments, the optical hardware configuration of the imaging system 200 may include the optical source 105, the beam splitter 110, the frequency shifter 115, the mirrors 120 and 125, the beam combiner 130, the polarizer 135 and the imaging sensor 140, albeit in a different configuration from that shown in FIG. 1. The imaging system 200 may further include an image data processor 180, which may be operably coupled to the imaging sensor 140. In some embodiments, the image data processor 180 may be external to the imaging system 200. Imaging system 200 may be employed to capture photons at the sensor 140, which generates related data to form an image of the target medium 170. Note that the placement of the mirrors and the imaging sensor is provided for conceptual purposes, but one of skill in the art would appreciate that the mirrors and the imaging sensor may be placed and oriented in any fashion to support the common path implementation described herein. Additionally, while the frequency shifter 115 is shown as acting upon the reference beam 150, one of skill in the art would appreciate that the frequency shifter 115 may alternatively be positioned to act upon the object beam 160.

In this regard, the optical source 105 may generate an optical beam that is directed to the beam splitter 110. Beam splitter 110 may split the beam into the reference beam 150 and an object beam 160. Additionally, the beam splitter 110 may generate the reference beam 150 and the object beam 160 such that the beams have relative orthogonal polarizations. The reference beam 150 may, according to some example embodiments, also be frequency shifted ($\Delta\omega$) by the frequency shifter 115. After the object beam interacts with the mirror 125 and the reference beam interacts with the mirror 120, the object beam 160 and the reference beam 150 may be combined by the beam combiner 130. According to some example embodiments, the combined beam 162 may be subjected to polarizer 135 so that components of the combined beam 162 (i.e., the reference beam 150 and the object beam 160) have a common polarization. In this regard, the polarizer 135 may be positioned between the beam combiner 130 and the target medium 170. After being combined and subjected to the polarizer 135, the combined polarized beam 163 may be exposed to the target medium 170 via a common path. The combined polarized beam 163 may pass through at least a portion of the target medium 170. Some photons of the combined polarized beam 163 may pass through the target medium 170 and some may be reflected by the target medium 170. According to some example embodiments, the photons that pass completely through the target medium 170 may be utilized for further analysis. Alternatively, or additionally, according to some example embodiments, the photons of the combined, polarized beam 163 that are reflected by the target medium 170 may be utilized for further analysis. Whether the pass through or the reflected photons are utilized may depend on the particular application and implementation (e.g., hardware implementation), and the photons leaving the target medium 170 may be referred to as the exposed beam, or the resultant common path interference beam, 163'. The combined polarized beam 163, which is a combination of the object beam 160 and the reference beam 150, may be routed (e.g., by the beam combiner 130 and/or other mirrors) along a common path into the target medium 170. Upon exposure with the target medium 170, target medium 170 may act upon the combined polarized beam 163 to scatter the photons of the beam 163, thereby forming a resultant common path interference beam 163', which may be received by the imaging sensor 140.

Because both the reference beam and the object beam components of the combined polarized beam 163 have been exposed to the target medium 170 via a common path (i.e., such that their respective photons propagate along approximately the same path), scattering, refractive index variations, and other effects associated with exposure to the target medium 170 have a similar impact on both the reference beam and the object beam components. As a result the relative phase error between the reference beam component and the object beam component of the common path interference beam 163' is relatively small. An illustration of the relative phase error is provided in FIG. 2a at 175 and 176, where 175 shows a representation of the reference beam component relative to a representation of the object beam component at 176 as compared to the imaging system 100 configuration. The resultant common path interference beam 163' from the target medium 170 may be received by the imaging sensor 140 and converted into common path interference beam data, which may be communicated to the image data processor 180 for analysis to generate, and possibly display or further transmit, related image data that describes the target medium 170.

According to various example embodiments, when using a common path approach with a target medium 170 that is a highly anisotropic material (e.g., tissue, water, etc . . . ), the probability that a photon will be forward scattered at a relatively small angle is high. Therefore, the common path approach can increase the quantity of photons (e.g., both ballistic and quasi-ballistic) incident on the imaging sensor 140, and that are included in the imaging analysis, because a smaller phase error is present between the reference and object beam components of the resultant common path interference beam 163. Therefore, more object and reference beam photons will meet the relative angular requirements and a higher number of photons can be used in a subsequent coherent mixing analyses. Because the number of photons considered in the analyses is higher, the signal to noise ratio can also be higher, as compared to the conventional ballistic (local oscillator) approach.

Additionally, with respect to the imaging system of FIG. 2a, according to some example embodiments, a common polarization technique may be utilized. In this regard, the placement of the polarizer 135 at a location prior to propagating the combined reference beam 150 and the object beam 160 into the target medium 170 causes the reference beam component and the object beam component of the combined polarized beam 163 to have a common relative optical polarization upon entry into the target medium 170. Such a common polarization approach, in association with the common path approach, further increases the probability that the object beam and reference beam components of the resultant common path interference beam 163' are scattered in the same direction when the components interact with the target medium 170. Accordingly, the increase in the number of object and reference beam photons with common scatter angles may also increase the number of photons that are coherently mixed, thereby increasing signal level and penetration depth.

Figure 2B:
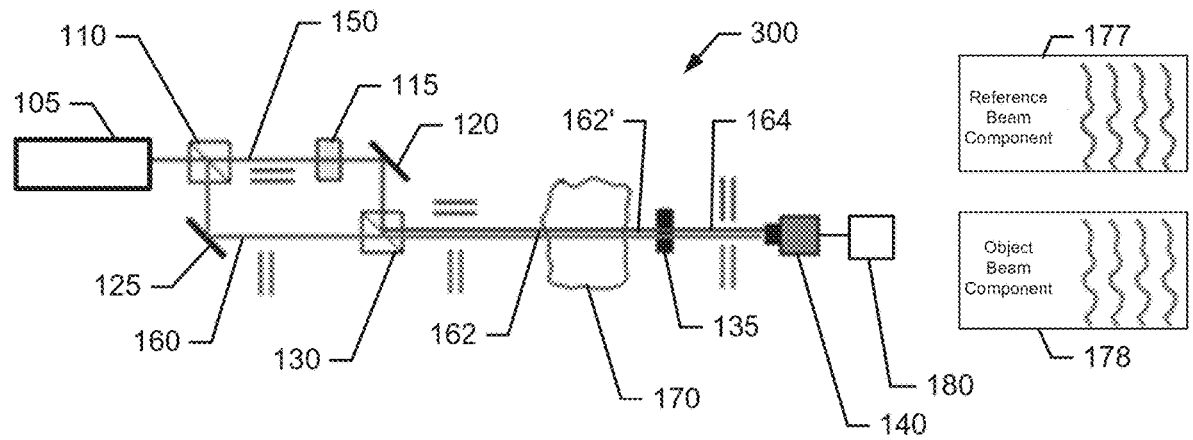
FIG. 2b illustrates a conceptual structure of an imaging system implementing a common path, cross polarization approach according to some example embodiments.

In contrast to the imaging system illustrated in FIG. 2a, FIG. 2b illustrates example embodiments of a conceptual imaging system 300 that is configured to implement a common path approach that utilizes a cross polarization, instead of a common polarization, technique. Again, because a common path approach is still being utilized with respect to the paths of the reference beam 150 and the object beam 160, the relative phase error is still minimized as described above with respect to FIG. 2a. In this regard, an illustration of the relative phase error is provided in FIGS. 2b at 177 and 178, where 177 shows a representation of the reference beam component relative to a representation of the object beam component at 178. However, rather than the polarizer 135 acting upon the combined reference beam 150 and object beam 160 prior to exposure to the target medium 170, the polarizer 135 in the approach of FIG. 2b may be placed such that it acts upon the combined beam 162 after having been exposed to the target medium 170. In other words, the polarizer 135 may be positioned between the target medium 170 and the imaging sensor 140. In this regard, the reference and object beam components of the combined beam 162 may have an orthogonal relative polarization prior to entering the target medium 170, and then after having interacted with the target medium 170, the polarizer 135 may interact with the exposed combined beam 162' to form a common path commonly polarized interference beam 164 for receipt by the imaging sensor 140. Imaging sensor 140 may generate data from the common path commonly polarized interference beam 164 for analysis by the image data processor 180.

In some embodiments, a total signal level received by the imaging sensor 140 using a cross polarization technique, as described with respect to FIG. 2b, may be less than the total signal level received using a common polarization technique, as described with respect to FIG. 2a. This is due at least in part because the probability of a photon scattering in a given direction may be a function of the photon's polarization. However, the likelihood of two photons scattering in the same direction is greatest when scattering occurs in the forward direction. This increased scattering likelihood in the forward direction may provide an increase in spatial resolution as compared to the common polarization approach as described in FIG. 2a.

Figure 4:
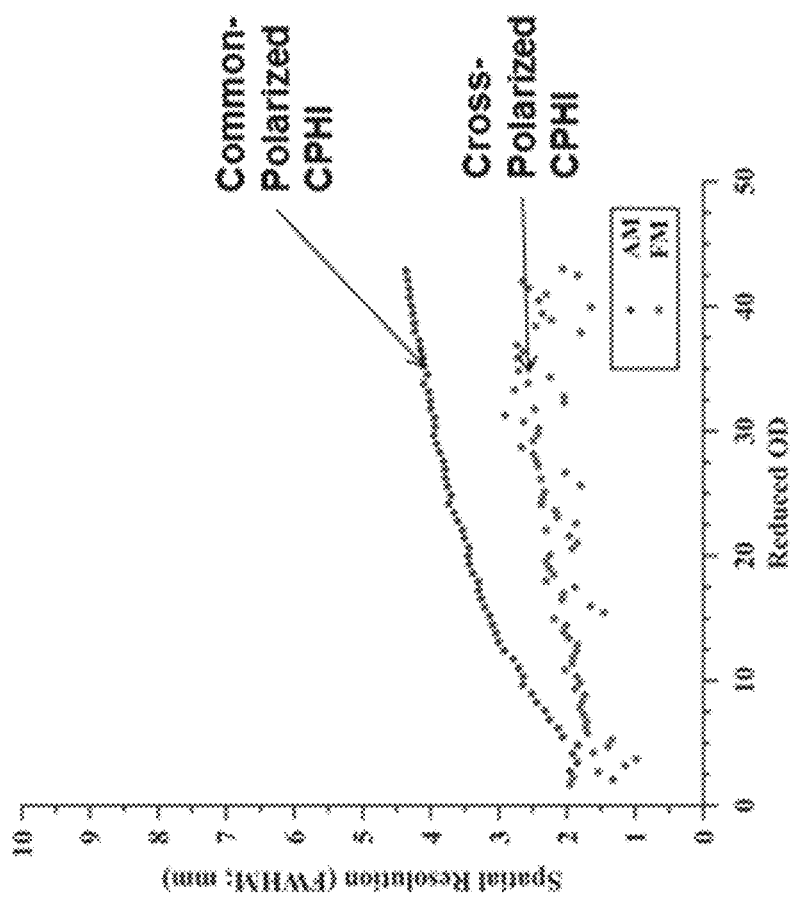
FIG. 4 is a chart of spatial resolution against reduced optical depth according to various example embodiments.
Figure 3:
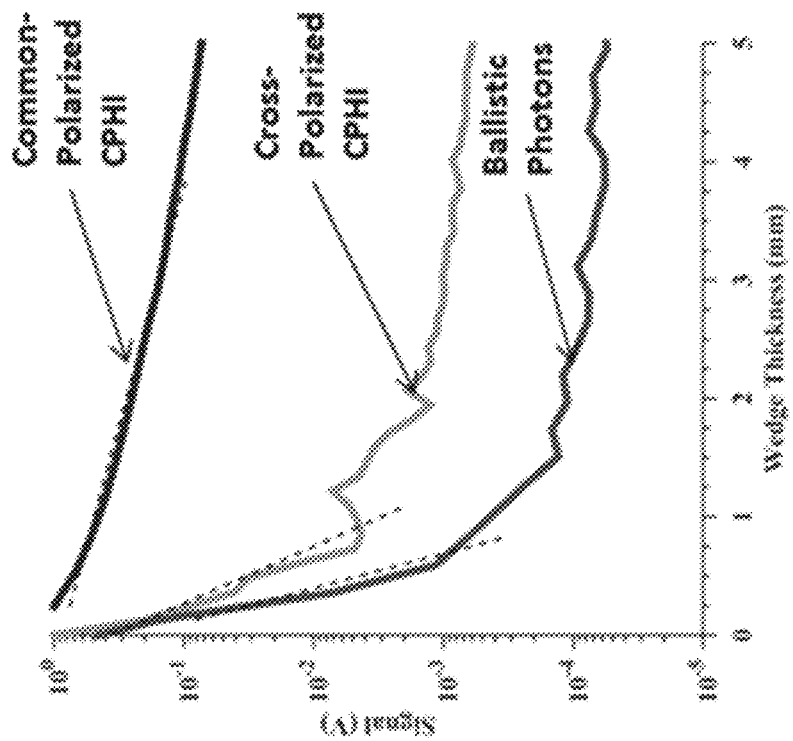
FIG. 3 is a chart that compares a common polarization approach with a cross polarization approach according to various example embodiments.

To better appreciate the differences in performance between the common path common polarization approach and the common path cross polarization approach, the charts of FIGS. 3 and 4 are provided. FIG. 3 provides a comparison of the common polarization approach, the cross polarization approach, and conventional ballistic photon approach with respect to the signal strength (in volts) and wedge thickness (in millimeters), or reduced optical depth (OD). The reduced optical depth represents the mean distance a photon will travel before it undergoes a scattering event. As an example, for a material with a scatter coefficient of 1 $mm^{-1}$, half of the photons are expected to undergo a scattering event every millimeter (which corresponds to one optical depth). As can be seen in FIG. 3, the common polarization approach may provide a relatively strong signal strength, but the cross polarized approach, while having a relative lower signal strength than the common polarized approach, may provide more detail/resolution in the signal. That said, with reference to FIG. 4, which charts spatial resolution (in millimeters) against reduced optical depth, it can be seen that the common polarized approach maintains a relatively constant spatial resolution as a function of reduced optical depth (also referred to as scattering depth). For context, optical depths of 30 to 50 correspond to the depths required to measure blood oxygen level detection (BOLD) signatures (e.g., 1 centimeter into the cortex) in neuroimaging applications. For comparison, the cross-polarized approach may provide a factor of two increase in spatial resolution (~2 mm versus ~4 mm) at 40 OD.

According to various example embodiments, the common path techniques described above may additionally frequency modulate either the reference beam or the object beam and allow for heterodyne detection. In this regard, frequency modulating the reference beam or the object beam can support the use of radio frequency mixing by the image data processor 180, since coherent mixing of the reference and object beams results in an amplitude modulated signal that can be extracted using radio frequency coherent detection techniques (e.g., a lock-in amplifier). Accordingly, the image data processor 180 may be configured to extract data indicative of this amplitude modulated signal from the data provided by the imaging sensor 140 that represents the common path interference beam received by the imaging sensor 140. Heterodyne detection can provide increased signal to noise ratios as a result of the radio frequency coherent processing gains, and it can also provide a technique to differentiate noise (or diffuse) photons from signal photons. Further, the common path imaging systems 200, 300 described above may also implement different frequency shifts on the reference beam 150 or the object beam 160, which may allow the image data processor 180 to analyze the received data to distinguish between different pairs of object and reference beams during electronic coherent processing.

As an alternative or in addition to using frequency modulation as provided above, various example embodiments may employ the use of optical IQ (in-phase and quadrature) demodulation by the image data processor 180 in systems with orthogonal polarizations for the object and reference beams, such as in the cross polarization approach described above. IQ demodulation can simplify the hardware and/or software of the optical transmitter (e.g., comprising the optical source 105 and the beam splitter 110) by not requiring the use of a frequency modulator. However, implementation of IQ demodulation may add complexity to the receiver design (e.g., comprising the imaging sensor 140 and the image data processor 180) since an optical IQ modulator design may be required. The processing of optical IQ demodulation can provide increased resolution over detecting only the in-phase or only the quadrature components. Further, as mentioned above, frequency and optical IQ demodulation can be combined in an imaging system as described herein to enhance the signal to noise ratio.

Further, the common path approaches described above and otherwise herein support the implementation of optical ranging. In this regard, by balancing the path lengths of the object and reference beams, an imaging system can support the use of optical sources (e.g., optical source 105) having short coherence lengths. As a result, low-cost and/or high-power optical sources such as, for example, Q-switched lasers, can be utilized with conventional range gating. The use of low-cost and/or high-power optical sources is in contrast to many conventional coherent optical imaging approaches that require long coherence length sources.

Various example embodiments of the common path approach described herein can be implemented and prove useful in a number of environments, including but not limited to medical imaging and neural tissue imaging or neuroimaging. With respect to neuroimaging in particular, example embodiments described herein may be implemented to perform BOLD. For example, while the common path approach may be implemented with a single optical source (e.g., laser) hardware configuration, to measure BOLD signatures two separate lasers may be utilized as with functional near-infrared spectroscopy (fNIRS) to measure a vascular response to the brain tissue's need for glucose. Such a differential approach can leverage the differences in absorption/scattering between oxygenated and de-oxygenated blood at select wavelengths, such as wavelengths above and below 800 nanometers (nm). In this regard, certain wavelengths may be of particular interest for neuroimaging. Measured responses from the visual cortex have shown that variations in the BOLD signature can occur at 780 nm and 852 nm. Conventional systems using fNIRS or functional magnetic resonance imaging (fMRI) have measured BOLD signatures at spatial resolution of approximately 1 centimeter (cm) and 1 to 3 millimeters (mm), respectively. However, as shown FIG. 4, example embodiments of the common path approach described herein can achieve spatial resolutions of less than 3 mm at equivalent depths.

Figure 5:
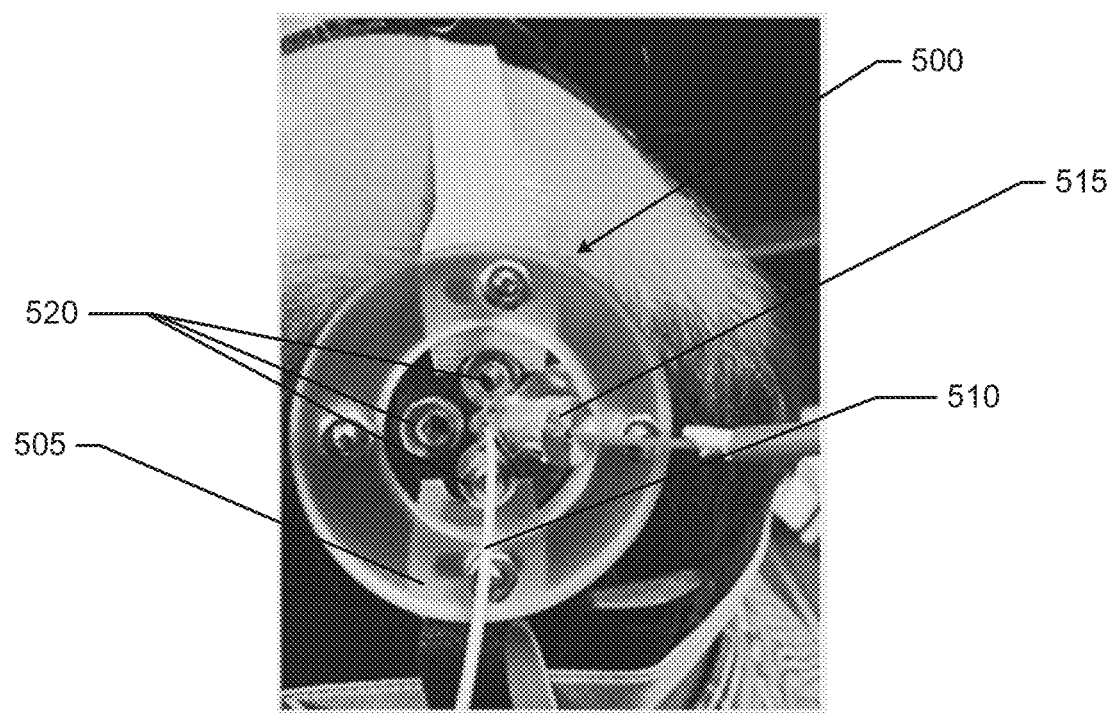
FIG. 5 is an image of optical hardware according to various example embodiments.
Figure 6:
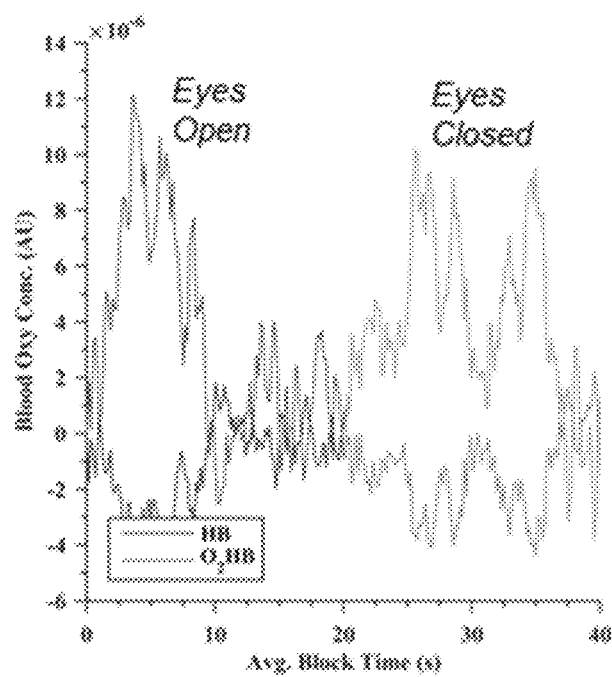
FIG. 6 is a chart of measurements of the blood oxygen concentration as a function of time according to various example embodiments.

FIG. 5 shows a picture of the optical hardware of an imaging system for implementation in neuroimaging according to various example embodiments. The optical hardware 500 may include a mount 505 to which an optical source 510 and an imaging sensor 515 may be affixed. According to various example embodiments, more than one imaging sensor 515 may be used, with the additional sensors being affixed to the mount 505 at positions 520. Using the optical hardware 500, BOLD signatures may be measured on the patient using example embodiments of the common path approach described herein. In this regard, the measurements of the visual cortex of the brain may be performed. FIG. 6 illustrates measurements of the blood oxygen concentration as a function of time. Variations in the measurements can be seen when the patient's eyes are open and closed.

In this regard, in relation to measuring optical activity, the Fast Optical Signal (FOS) can be measured. The FOS can occur due to changes in the scattering properties of neural tissue that correlate with localized activity. As such, use of two-color imaging may not provide a benefit in FOS detection, since the FOS is not associated with a vascular response. Detection of the FOS, however, can be accomplished by measuring changes in absorption/scattering of the neural tissue, such as via the common path approach described in association with various example embodiments.

With respect to the optical hardware of the example imaging systems described herein, examples of the optical source (which may also be referred to as the optical transmitter) may be further described. In this regard, the optical source may be a packaged laser that directly illuminates the surface of the skin or, according to some example embodiments, the optical source may include an optical fiber that is configured to route the desired light beam to the area of interest. Whether or not an optical fiber is used, according to some example embodiments, minimizing the beam diameter into the brain tissue, such as by focusing the beam, can be advantageous for capturing ballistic and quasi-ballistic photons, which in turn maximizes optical speckle size at the detection surface of the imaging sensor, and therefore maximizes coherent mixing efficiency. Further, spatial resolution can be dictated by separation of transmit apertures and beam diameters with multiple transmit apertures improving the two dimensional image quality. As such, discrete measurements may be taken which may limit spatial resolution to approximately 1 to 2 mm due to physical limits in minimizing separation between the sources or transmitters. Further, according to some example embodiments, speckle that is modulated at the frequency shift introduced by the frequency shifter may be received as a result of the ballistic and quasi-ballistic photons, which facilitates the ability to discriminate speckle due to noise or diffuse photons.

With respect to the optical hardware of the example imaging systems described herein, examples of the imaging sensor 140 (which may also be referred to as the optical receiver) may be further described. In this regard, the imaging sensor 140 may include a bare detector or be operatively coupled with an optical fiber that may be used in association with the imaging sensor 140. For a mono-static configuration, an optical fiber may be used with the transmit beam and then a return signal including the reference and object beams may be separated using appropriate optics, such as splitters, combiners, mirrors, etc. For a bi-static configuration, one or more sensors may be used to detect the returned object and reference beams that carry information about object. In this regard, the number and size of detectors may determine the detected signal level.

Additionally, use of an optical fiber with the imaging sensor 140 may provide reduced field-of-view (FOV) dictated by a free-space optical coupler which can minimize background noise photons but may also require increased pointing accuracy such that FOV overlaps the desired measurement volume. The diameter of a fiber coupler can be optimized to support an expected speckle size. Alternatively, a bare detection surface of an imaging sensor 140 may provide increased FOV and minimized package size. An increased FOV can alleviate the need for accurate pointing to achieve overlap between desired measurement volume and detector FOV. The sensor size may be optimized to support an expected speckle size. However, the signatures may degrade with an increase in speckle across the detector surface of the sensor 140. A bare detector can also increase the signal to noise ratio since fiber coupling efficiency need not be considered.

FIGS. 7a and 7b illustrate example optical hardware 700 for a fixed depth implementation with multiple sensors. FIG. 7a provides a side cross section view of the optical hardware configuration 700. According to some example embodiments, the hardware configuration 700 may include an imaging system 750, which may be similar to the imaging systems 200 or 300, or as otherwise described herein, and a mount 705. Additionally, while the imaging system 750 is shown located on top of the mount 705 in FIG. 7a, in other embodiments the imaging system 705 may be integrated within the mount 705, or otherwise located with respect to the mount 705.

In this regard, the mount 705 may be configured to house and maintain the positioning of the optical source and the imaging sensors. The mount 705 may include a transmit slot 710 that is configured to receive an optical fiber and/or a gradient index lens through which the optical source beam 701 generated in accordance with various example embodiments may be provided to the target medium 735 (e.g., neural tissue). According to some example embodiments, the transmit slot 710 may have a diameter 715 of approximately 2.8 mm. The mount 705 may also include receiver slots 720a and 720b for respective imaging sensors and associated optical lenses (not shown). Based on the spacing of the receiver slots 720a and 720b from the transmit slot 710 and a desired depth, a respective angle θ and a respective offset may be defined for each receiver slot 720a, 720b. Return signals 702a and 702b resulting from the optical source beam 701 scattering or reflecting from the target medium 735 may propagate through a respective receiver slot 720a, 720b to be received by a respective imaging sensor. As can be seen in FIG. 7a, the depth of the measurement into the target medium 735 can be determined based on the placement of the imaging sensors and the respective angle θ. Further, according to various example embodiments, a distance 725 between the mount 705 and the target medium 735 may be defined, and according to some example embodiments, the distance 725 may be approximately 5 mm. In some embodiments, the distance 725 may be representative of the cumulative thickness of the skin, skull, and potentially other biological matter of a human head. Similarly, based on the desired depth for the measurement, a distance 730 into the target medium 735 may be defined, and according to some example embodiments, the distance 730 may be approximately 12 mm. One of skill in the art will appreciate that the distances and angles provided herein are merely provided as examples for reference and comprehension. Therefore, the scope of the related example embodiments is not limited to these distances.

Referring to FIG. 7b, a top cross section of the optical hardware 700 is provided. In this regard, the mount 705 may include a plurality of receive barrels 745, each being associated with a respective imaging sensor 740a, 740b, 740c, 740d and a respective receiver slot. Each of the imaging sensors may be offset from the transmit slot 710 by an offset distance $d_{offset}$ and may have a given angle θ to define the sensor position in the mount 705. By way of example, imaging sensor 740a may have an offset distance of approximately 3 mm and an angle θ of approximately 10°. Imaging sensor 740b may have an offset distance of approximately 4 mm and an angle θ of approximately 13°. Imaging sensor 740c may have an offset distance of approximately 6 mm and an angle θ of approximately 19°. Imaging sensor 740d may have an offset distance of approximately 8 mm and an angle θ of approximately 25°. In this regard, it is noteworthy that each imaging sensor's offset and angle can be different.

Figure 8B:
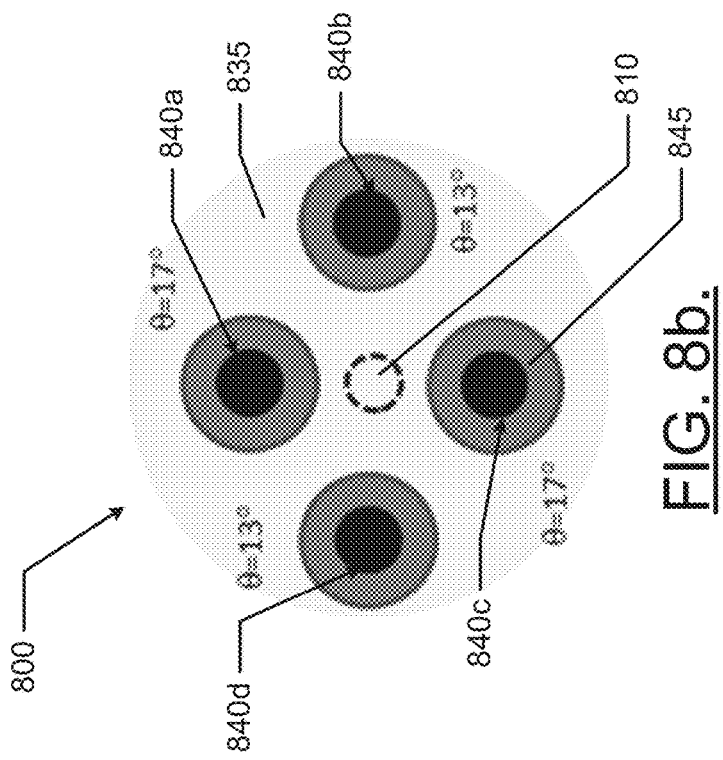
FIGS. 8a and 8b illustrate example optical hardware for multiple depth measurements according to various example embodiments.
Figure 8A:
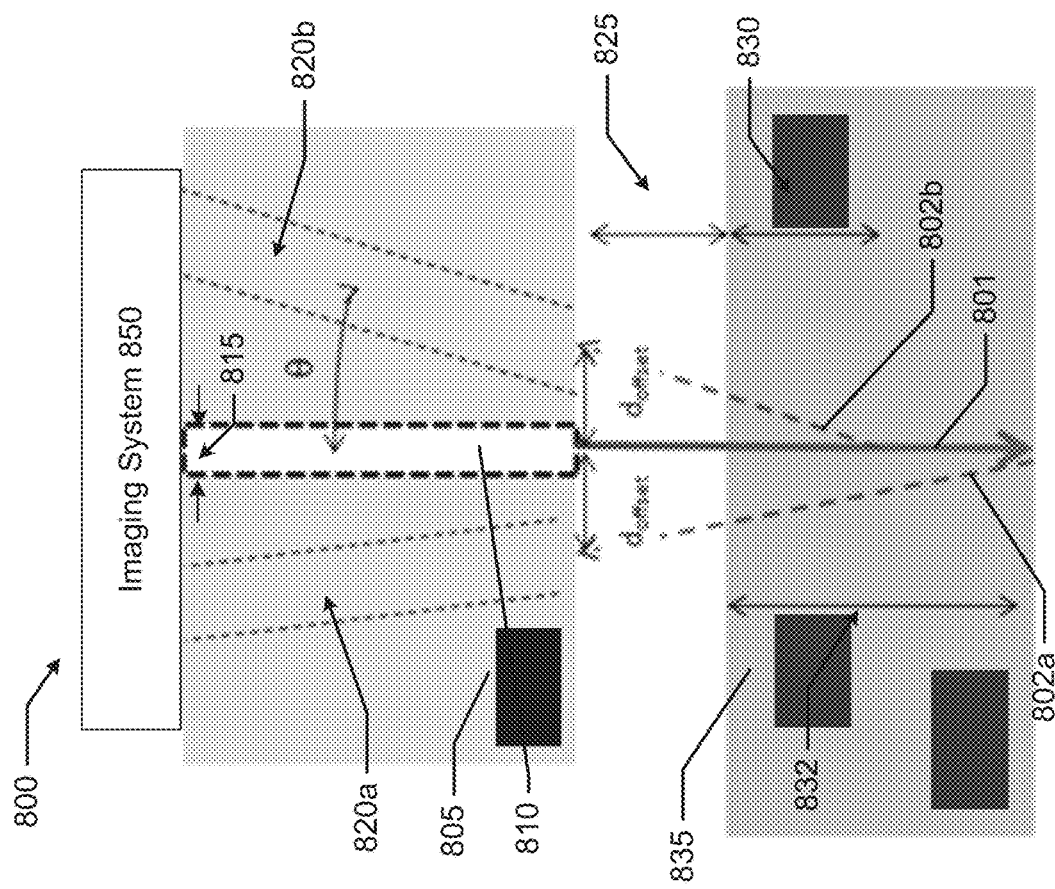

FIGS. 8a and 8b illustrate example optical hardware 800 for a multiple depth implementation with multiple imaging sensors. FIG. 8a provides a side cross section view of the optical hardware 800. According to some example embodiments, the hardware configuration 800 may include an imaging system 850, which may be similar to the imaging systems 200 or 300, or as otherwise described herein, and a mount 805. Additionally, while the imaging system 850 is shown located on top of the mount 805 in FIG. 8a, in other embodiments the imaging system 850 may be integrated within the mount 805, or otherwise located with respect to the mount 805.

In this regard, the mount 805 may be configured to house and maintain the positioning of the optical source and the imaging sensors. The mount 805 may include a transmit slot 810 that is configured to receive an optical fiber and/or a gradient index lens through which the optical source beam 801 may be generated in accordance with various example embodiments and may be provided to the target medium 835 (e.g., neural tissue). According to some example embodiments, the transmit slot 810 may have diameter 815 of 2.8 mm. The mount 805 may also include receiver slots 820a and 820b for respective imaging sensors and associated optical lenses (not shown). Based on the spacing of the receiver slots 820a and 820b from the transmit slot 810 and the desired multiple depths, a respective angle θ and a respective offset $d_{offset}$ may be defined for each receiver slot 820a, 820b. Return signals 802a and 802b resulting from the optical source beam 801 scattering or reflecting from the target medium 835 may propagate through a respective receiver slot 820a, 820b to a respective imaging sensor. As can be seen in FIG. 8a, the depth of the respective measurement can be determined based on the placement of the imaging sensors and the respective angle θ. Further, according to various example embodiments, a distance 825 between the mount 805 and the target medium 835 may be defined, and according to some example embodiments, the distance 825 may be approximately 5 mm. Similarly, based on the multiple desired depths for measurement, a distance 830 into the target medium 835 may be defined, and according to some example embodiments, the distance 830 may be approximately 8 mm. Further, a distance 832 into the target medium 835 may be defined, and according to some example embodiments, the distance 832 may be approximately 12 mm.

Referring to FIG. 8b, a top cross section of the optical hardware 800 is provided. In this regard, the mount 805 may include a plurality of receive barrels 845, each being associated with a respective imaging sensor 840a, 840b, 840c, 840d and a respective receiver slot. Each of the imaging sensors may be offset from the transmit slot 810 by an offset distance and may have a given angle θ to define the imaging sensor position in the mount 805. According to some example embodiments, more than one imaging sensor may be positioned at the same distance and angle relative to the transmit slot 810 to provide redundancy in measurements. By way of example, imaging sensor 840a may have an offset distance of approximately 4 mm and an angle θ of approximately 17°. Imaging sensor 840b may have an offset distance of approximately 8 mm and an angle θ of approximately 13°. Imaging sensor 840c may have an offset distance of approximately 4 mm and an angle θ of approximately 17°. Imaging sensor 840d may have an offset distance of approximately 8 mm and an angle θ of approximately 13°. In this regard, it is noteworthy that some of the sensors may be positioned such that there is redundancy in their measurements based on offset distances and orientation angles.

The common path approach that has been described herein can also be implemented in conjunction with Fresnel zone sensing techniques. In this regard, the common path approach, in accordance with various example embodiments, may be modified by changing the relative beam curvature of the reference beam in relation to the object beam, or by changing the curvature of the object beam in relation to the reference beam, either of which forms a Fresnel zone. An image can be reconstructed by scanning the Fresnel zone over the object and then using matched filter processing to reconstruct the original object. Image resolution may be dictated by the size of the smallest ring (fringe) in the Fresnel zone. Scanning the Fresnel zone can provide a significant increase in area rate coverage, in comparison to scanning a beam with a diameter equal to the width of the smallest ring of the Fresnel zone. With respect to this approach, ranging can be accomplished using conventional ranging techniques such as time-of-flight with a pulsed laser or amplitude modulation and then correlating phase lag to range.

Figure 9:
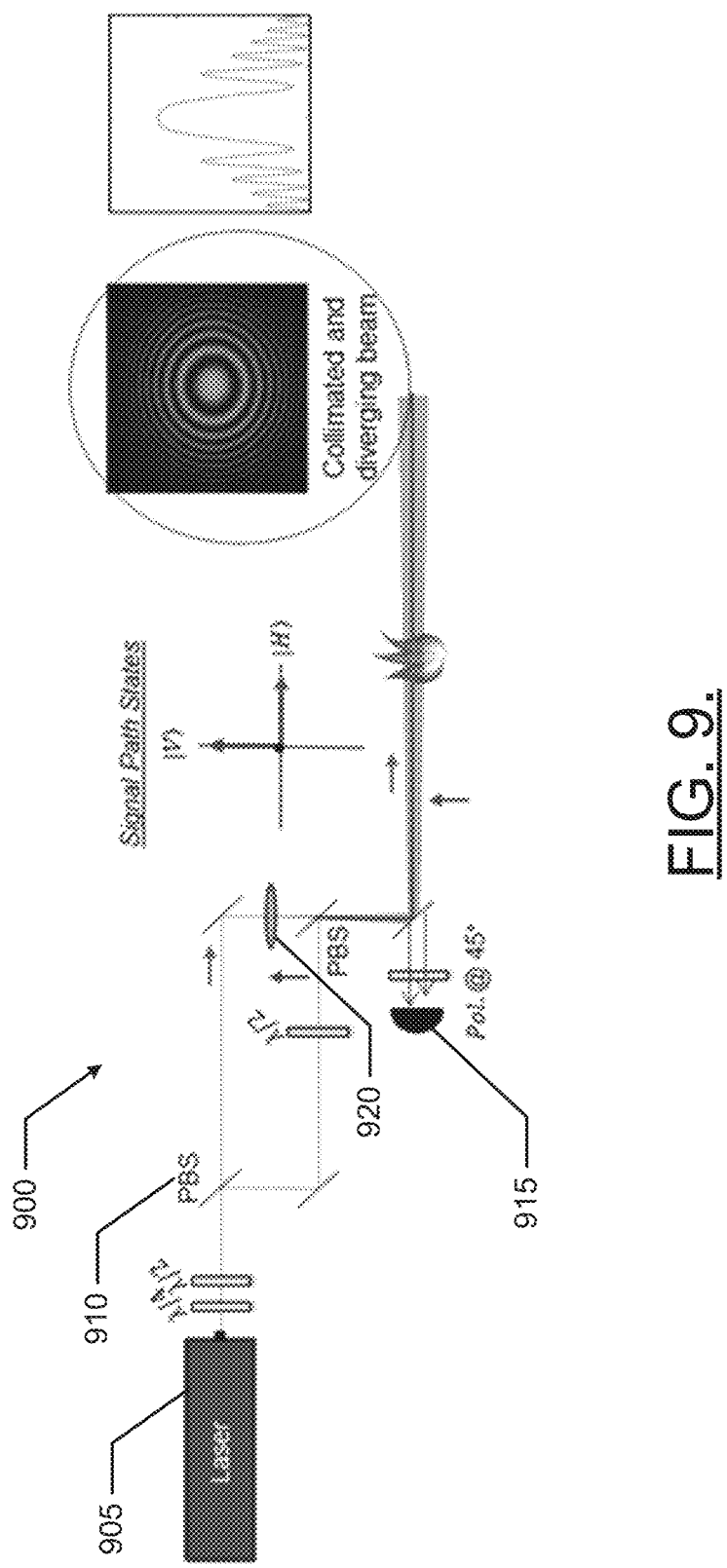
FIG. 9 illustrates an example conceptual structure of an imaging system for generating Fresnel zones according to various example embodiments.

FIG. 9 provides an illustration of an example conceptual structure of an imaging system 900 for generating Fresnel zones. In this regard, the laser 905, which may be one type of optical source, may generate a beam that is then frequency shifted and spilt into a reference beam and an object beam by a polarizing beam splitter 910. The lens 920 may assist in the generation of the Fresnel zone by diverging one of the beams generated by the polarizing beam splitter 910. The beam is ultimately received at the imaging sensor 915 in the form of a collimated and diverging beam.

The Fresnel zone can be leveraged for use in a scanning process by scanning the Fresnel zone over a very small orifice (e.g., a pinhole). In this regard, according to some example embodiments, the field of view of the imaging sensor may be limited to a maximum scan angle. Further, both cross-correlation and deconvolution image reconstruction algorithms may be implemented. Reflection mode measurements may also be utilized to prepare measurements and more specifically, neuroimaging measurements.

Figure 10:
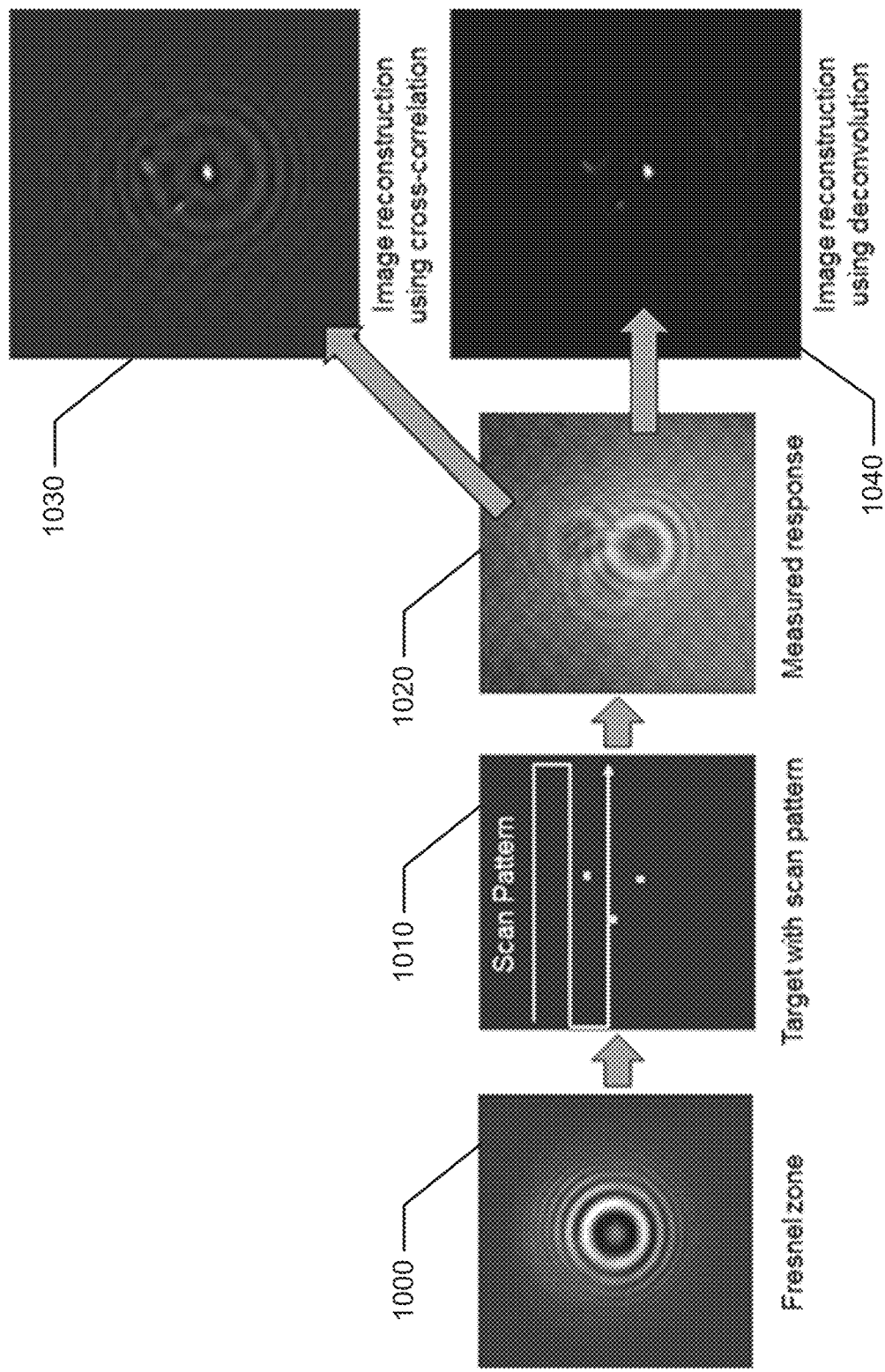
FIG. 10 illustrates an example process for using Fresnel zones in a scanning technique according to various example embodiments.

One example process of using a Fresnel zone scanning technique is provided in FIG. 10. In this regard, the Fresnel zone may be generated at 1000, as described above. At 1010, the Fresnel zone may be applied to a scan pattern for a target. A measured response may be received at 1020. At 1030, image reconstruction can be performed using cross-correlation. Further, at 1040, image reconstruction can be performed using deconvolution.

Figure 11:
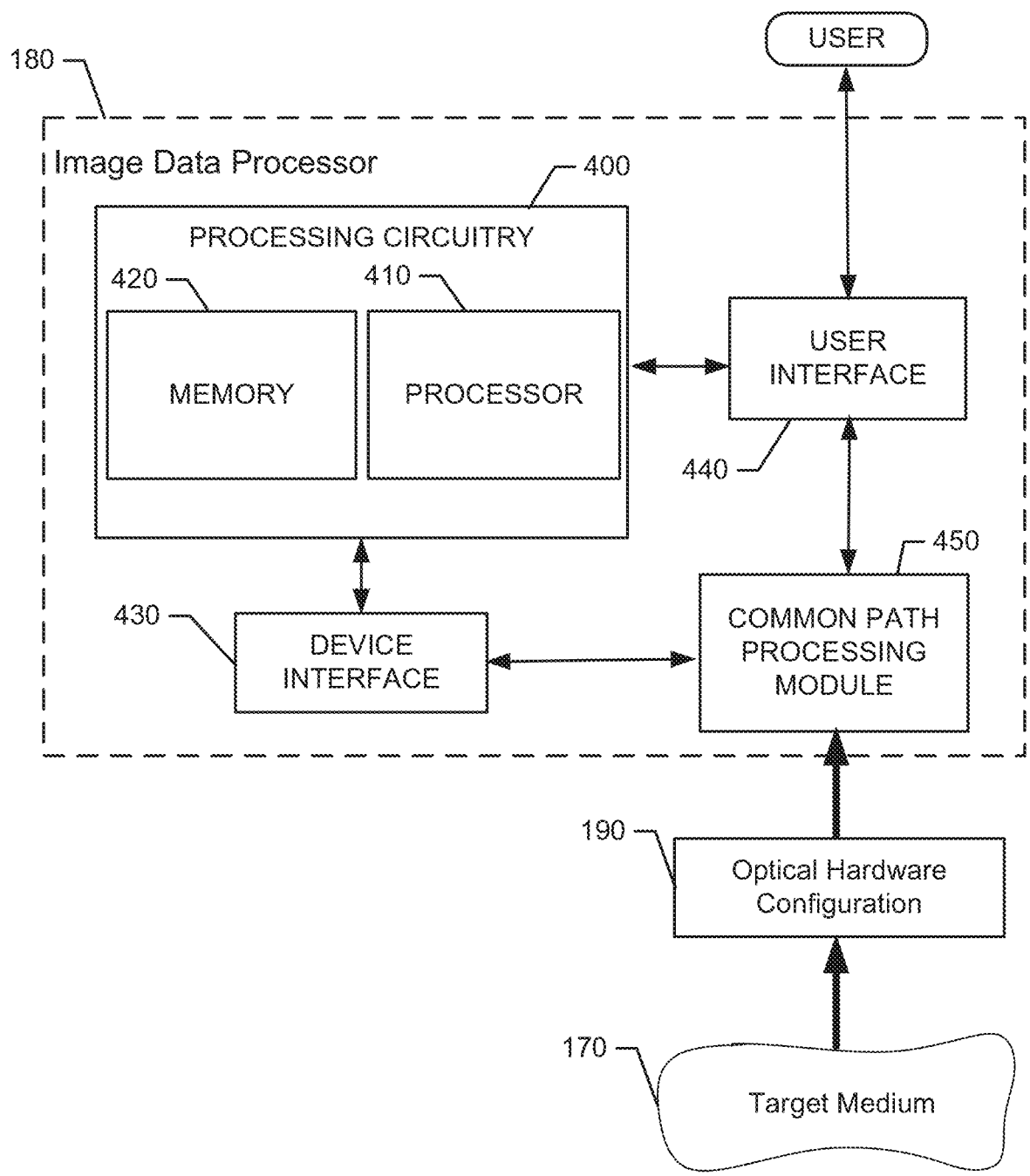
FIG. 11 illustrates a block diagram of an imaging system according to various example embodiments.

FIG. 11 illustrates a block diagram of an imaging system according to various example embodiments with added detail regarding the construction and operation of the image data processor 180. The data associated with performing image processing techniques based on a common path approach as provided herein may be distinctly processed by the image data processor 180. The data processed by the image data processor 180 may be provided by the optical hardware configuration 190. In this regard, the optical hardware configuration 190 may be any one of the optical hardware configurations described with respect to imaging systems 200 and 300, as well as modifications to these imaging systems as described with respect to FIGS. 2a to 10, and otherwise herein.

In this regard, the image data processor 180 may include or otherwise be in communication with processing circuitry 400 that is configurable to perform actions in accordance with example embodiments described herein. As such, for example, at least some of the functions attributable to the image data processor 180 may be carried out by or otherwise instructed by the processing circuitry 400. The processing circuitry 400 may therefore provide the hardware for hosting software to configure the system for analysis techniques consistent with example embodiments. Detection of neural signatures and corresponding imaging and/or functions driven based on such signatures may then be accomplished using the processing circuitry 400.

The processing circuitry 400 may be configured to perform data processing, control function execution and/or other processing and management services according to various example embodiments. In some example embodiments, the processing circuitry 400 may be embodied as a chip or chip set. In other words, the processing circuitry 400 may comprise one or more physical packages (e.g., chips) including materials, components and/or wires on a structural assembly (e.g., a baseboard).

In an example embodiment, the processing circuitry 400 may include one or more instances of a processor 410 and memory 420 that may be in communication with or otherwise control a device interface 430 and, in some cases, a user interface 440. As such, the processing circuitry 400 may be embodied as one or more instances of a circuit chip (e.g., an integrated circuit chip) configured (e.g., with hardware, software or a combination of hardware and software) to perform operations described herein.

The user interface 440 (if implemented) may be in communication with the processing circuitry 400 to receive an indication of a user input at the user interface 440 and/or to provide an audible, visual, mechanical or other output to the user. As such, the user interface 440 may include, for example, a display, printer, one or more buttons or keys (e.g., function buttons), and/or other input/output mechanisms (e.g., keyboard, touch screen, mouse, microphone, speakers, cursor, joystick, lights and/or the like). The user interface 440 may display information such as an image data including, but not limited to, a neural signature or certain characteristics of a data set (e.g., including images or results of analyzing images) being processed by the image data processor 180. The image data or characteristics of the data set may then be processed and information associated therewith may be presented on a display of the user interface 440 based on instructions executed by the processing circuitry 400 for the analysis of the data according to prescribed methodologies and/or algorithms. Moreover, in some cases, the user interface 440 may include options for selection of one or more reports or displays to be generated based on the analysis of a given data set.

The device interface 430 may include one or more interface mechanisms for enabling communication with other external devices (e.g., output devices, input devices and/or the like) or internal functional components of the detection system. In some cases, the device interface 430 may be any means such as a device or circuitry embodied in either hardware, or a combination of hardware and software that is configured to receive and/or transmit data from/to devices in communication with the processing circuitry 400.

In an exemplary embodiment, the memory 420 may include one or more non-transitory memory devices such as, for example, volatile and/or non-volatile memory that may be either fixed or removable. The memory 420 may be configured to store information, data, applications, instructions or the like for enabling the image data processor 180 to carry out various functions in accordance with example embodiments of the present invention. For example, the memory 420 could be configured to buffer input data for processing by the processor 410. Additionally or alternatively, the memory 420 could be configured to store instructions for execution by the processor 410. As yet another alternative or additional feature, the memory 420 may include one or more databases that may store a variety of data sets indicative of patterns that are configured to trigger specific responses or algorithms, image data processing techniques, processing algorithms and/or the like to be employed for the execution of example embodiments. Among the contents of the memory 420, applications may be stored for execution by the processor 410 in order to carry out the functionality associated with each respective application. In some cases, the applications may include directions for control of the image data processor 180 to process data received from the optical hardware configuration 190.

In particular, in some cases, the applications may include instructions for directing operation of a common path processing module 450 relative to image data received from the optical hardware configuration 190.

The processor 410 may be embodied in a number of different ways. For example, the processor 410 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 410 may be configured to execute instructions stored in the memory 420 or otherwise accessible to the processor 410. As such, whether configured by hardware or by a combination of hardware and software, the processor 410 may represent an entity (e.g., physically embodied in circuitry—in the form of processing circuitry 400) capable of performing operations according to embodiments of the present invention while configured accordingly. Thus, for example, when the processor 410 is embodied as an ASIC, FPGA or the like, the processor 410 may be specifically configured hardware for conducting the operations described herein. Alternatively, as another example, when the processor 410 is embodied as an executor of software instructions, the instructions may specifically configure the processor 410 to perform the operations described herein.

In an example embodiment, the processor 410 (or the processing circuitry 400) may be embodied as, include or otherwise control the image data processor 180. As such, in some embodiments, the processor 410 (or the processing circuitry 400) may be said to cause each of the operations described in connection with the image data processor 180 and/or the common path processing module 450 by directing the image data processor 180 and/or the common path processing module 450 to undertake the corresponding functionalities responsive to execution of instructions or algorithms configuring the processor 410 (or processing circuitry 400) accordingly.

The common path processing module 450 may be configured to process image data received from the optical hardware configuration 190, and more specifically an imaging sensor of the optical hardware configuration 190. Further, the common path processing module 450 may be configured to analyze common path interference beam data to generate image data describing a target medium. In this regard, an optical source of the optical hardware configuration 190 may be configured to generate an optical beam. Further, a beam splitter of the optical hardware configuration 190 may be configured to split the optical beam into a reference beam and an object beam. Subsequently, a beam combiner of the optical hardware configuration 190, positioned to receive the reference beam and the object beam, may be configured to route the reference beam and the object beam along a common path into a target medium. The target medium may act upon the reference beam and the object beam to form a common path interference beam. The optical hardware configuration 190 may further comprise an imaging sensor configured to receive the common path interference beam and generate common path interference beam data associated with the common path interference beam, and provide the data to the common path processing module 450 for processing.

According to some example embodiments, the data provided to the common path imaging module 450 may be provided via a polarizer configured to polarize the reference beam and the object beam to have a common relative optical polarization prior to entering the target medium. According to some example embodiments, the data provided to the common path imaging module 450 may be provided via a polarizer configured to polarize the reference beam and the object beam to have an orthogonal relative optical polarization prior to entering the target medium. In some example embodiments, the common path processing module 450 may be further configured to perform in-phase and quadrature demodulation on the common path interference beam data. According to some example embodiments, the data provided to the common path imaging module 450 may be provided via a frequency shifter configured to shift a frequency of the reference beam or shift a frequency of the object beam. In this regard, the common path imaging module 450 may be further configured to extract data for an amplitude modulated signal from the common path interference beam data using heterodyne detection. According to some example embodiments, the data provided to the common path imaging module 450 may be provided via an optical source, where the optical source comprises a short coherence length laser. Further, the optical source may be configured to generate the optical beam in the form of a pulsed beam. According to some example embodiments, the target medium can be neural tissue. According to some example embodiments, the data provided to the common path imaging module 450 may be provided via an optical fiber operably connected to the optical source and configured to transmit the optical beam. According to some example embodiments, the data provided to the common path imaging module 450 may be provided via a plurality of imaging sensors, where each imaging sensor generates respective common path interference beam data to be provided to the common path imaging module 450 and image data processor 180. According to some example embodiments, the data provided to the common path imaging module 450 may be provided via a beam splitter that is further configured to change a relative beam curvature between the reference beam and the object beam. In this regard, the common path imaging module 450 may be further configured to analyze the common path interference beam data to generate image data describing the target medium in the form of a Fresnel zone pattern.

Figure 12:
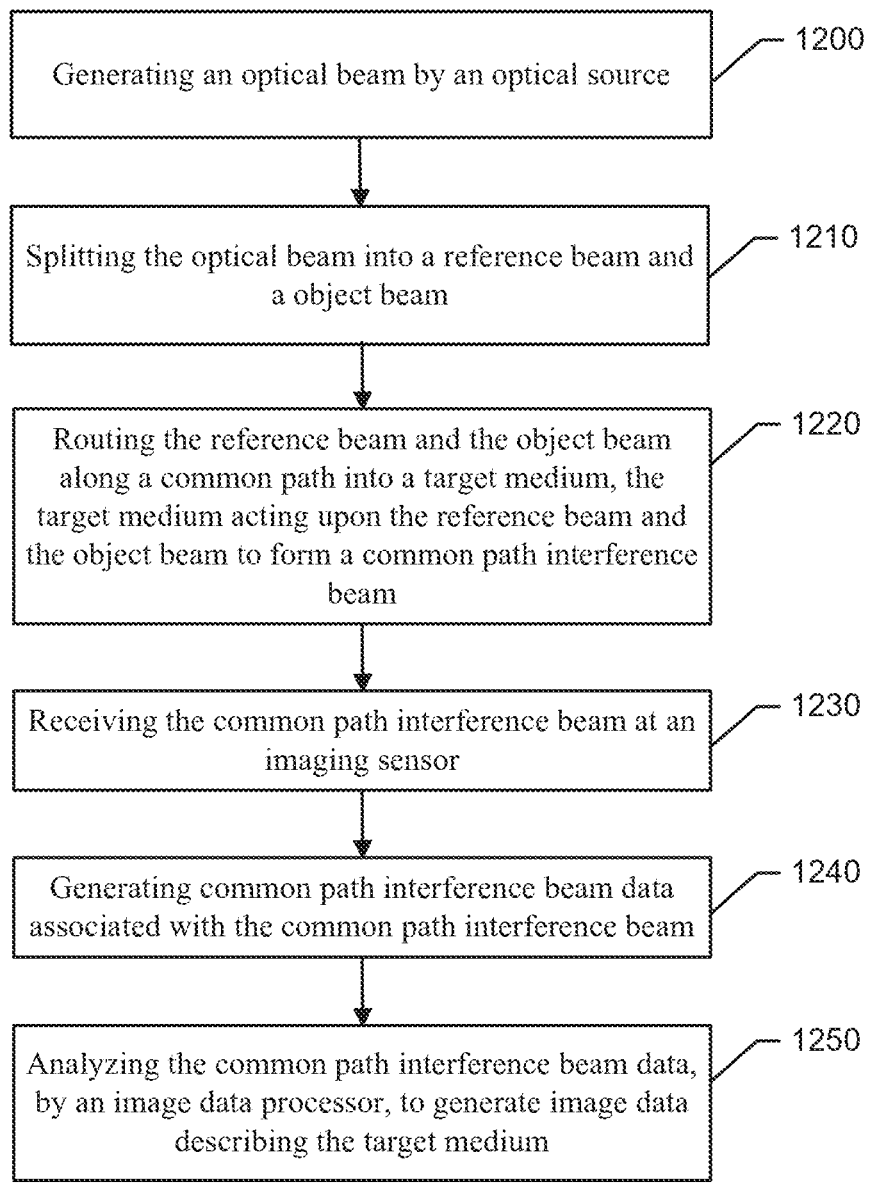
FIG. 12 shows an exemplary block diagram of a method according to various example embodiments.

FIG. 12 is a flowchart of a method and program product according to various example embodiments. It will be understood that each block of the flowchart, and combinations of blocks in the flowchart, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device of a sensor, electrode or processing circuitry associated therewith and executed by a processor in the sensor, electrode or processing circuitry associated therewith. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method of generating an image according to some example embodiments is shown in FIG. 12. The method of FIG. 12 may entirely, or at least in part, be executed automatically (e.g., without operator interaction to initiate each step or the series of steps) by processing circuitry. The method may include generating an optical beam by an optical source at operation 1200. The method may further include splitting the optical beam into a reference beam and an object beam at operation 180 at operation 1210. At operation 1220, the method may include routing the reference beam and the object beam along a common path into a target medium. In this regard, the target medium may act upon the reference beam and the object beam to form a common path interference beam. Further, the method may include receiving the common path interference beam at an imaging sensor at operation 1230. At operation 1240, the method may include generating common path interference beam data associated with the common path interference beam, and at operation 1250, the method may include analyzing the common path interference beam data, by an image data processor, to generate image data describing the target medium.

In some embodiments, additional optional operations may be included or the operations described above may be modified or augmented. Each of the additional operations, modification or augmentations may be practiced in combination with the operations above and/or in combination with each other. Thus, some, all or none of the additional operations, modification or augmentations may be utilized in some embodiments. In an example embodiment, the example method may further include polarizing the reference beam and the object beam to have a common relative optical polarization prior to entering the target medium. Alternatively, according to some example embodiments, the example method may further include polarizing the reference beam and the object beam to have an orthogonal relative optical polarization prior to entering the target medium. Additionally or alternatively, the example method may further comprise performing in-phase and quadrature demodulation on the common path interference beam data. According to some example embodiments, the example method may additionally or alternatively include shifting a frequency of the reference beam or shifting a frequency of the object beam and extracting an amplitude modulated signal from the common path interference beam using heterodyne detection. Further, according to some example embodiments, generating the optical beam may comprise generating the optical beam in the form of a pulsed beam via a short coherence length laser. According to some example embodiments, the target medium may be neural tissue. The example method may additionally or alternatively include transmitting the optical beam via an optical fiber operably connected to the optical source. According to some example embodiments, the example method may additionally or alternatively include changing a relative beam curvature between the reference beam and the object beam and analyzing the common path interference beam data to generate the image data describing the target medium in the form of a Fresnel zone pattern.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. An imaging system comprising:
an optical source configured to generate an optical beam;
a beam splitter configured to split the optical beam into a reference beam and an object beam, wherein the reference beam and the object beam are output from the beam splitter such that a reference beam polarization of the reference beam is different from an object beam polarization of the object beam;
a frequency shifter configured to shift a frequency of one of the reference beam or the object beam;
a beam combiner positioned to receive the reference beam and the object beam, combine the reference beam with the object beam to form a combined beam, and route the combined beam having a reference beam component and an object beam component directed along a common path into a target medium, the target medium acting upon the combined beam to form a common path interference beam;
a polarizer configured to polarize the combined beam or the common path interference beam;
an imaging sensor disposed downstream from the polarizer, the image sensor being configured to receive the common path interference beam and generate common path interference beam data associated with the common path interference beam; and an image data processor configured to analyze the common path interference beam data to generate image data describing the target medium.

2. The imaging system of claim 1 wherein the polarizer is positioned to polarize the combined beam prior to interaction with the target medium.

3. The imaging system of claim 1 wherein the polarizer is positioned to polarize the common path interference beam after interaction with the target medium.

4. The imaging system of claim 3 wherein the image data processor is further configured to perform in-phase and quadrature demodulation on the common path interference beam data.

5. The imaging system of claim 1 wherein the image data processor is further configured to extract data for an amplitude modulated signal from the common path interference beam data using heterodyne detection.

6. The imaging system of claim 1 wherein the optical source comprises a short coherence length laser, and the optical source is configured to generate the optical beam in the form of a pulsed beam.

7. The imaging system of claim 1 further comprising a mount, wherein the optical source and the imaging sensor are affixed to the mount; and wherein the imaging sensor is configured to receive the common path interference beam after interaction with the target medium comprising neural tissue.

8. The imaging system of claim 1 further comprising an optical fiber operably connected to the optical source, wherein the optical fiber is configured to transmit the optical beam.

9. The imaging system of claim 1 further comprising a plurality of imaging sensors including the imaging sensor, wherein each imaging sensor generates respective common path interference beam data to be provided to the image data processor.

10. The imaging system of claim 1 wherein the image data processor is configured to analyze the common path interference beam data to generate image data describing the target medium in the form of a Fresnel zone pattern.

11. A method comprising:
generating an optical beam by an optical source;
splitting the optical beam by a beam splitter into a reference beam and an object beam, wherein the reference beam and the object beam are output from the beam splitter such that a reference beam polarization of the reference beam is different from an object beam polarization of the object beam;
frequency shifting one of the reference beam or the object beam;
combining the reference beam with the object beam to form a combined beam;
routing the combined beam along a common path into a target medium, the target medium acting upon the combined beam to form a common path interference beam;
polarizing, by a polarizer, the combined beam or the common path interference beam;
receiving the common path interference beam at an imaging sensor disposed downstream from the polarizer;
generating common path interference beam data associated with the common path interference beam; and
analyzing the common path interference beam data, by an image data processor, to generate image data describing the target medium, wherein analyzing the common path interference beam data includes coherently mixing the common path interference beam data for the object beam and the common path interference beam data for the reference beam.

12. The method of claim 11 further comprising polarizing the combined beam prior to entering the target medium.

13. The method of claim 11 further comprising polarizing the common path interference beam after interaction with the target medium.

14. The method of claim 13 wherein the analyzing further comprises performing in-phase and quadrature demodulation on the common path interference beam data.

15. The method of claim 11 further comprising extracting data for an amplitude modulated signal from the common path interference beam using heterodyne detection.

16. The method of claim 11 wherein generating the optical beam comprises generating the optical beam in the form of a pulsed beam by a short coherence length laser.

17. An apparatus comprising:
a mount comprising a transmit slot and a receiver slot;
an optical source configured to generate an optical beam;
a beam splitter configured to split the optical beam into a reference beam and an object beam, wherein the reference beam and the object beam are output from the beam splitter such that a reference beam polarization of the reference beam is different from an object beam polarization of the object beam;
a frequency shifter configured to shift a frequency of one of the reference beam or the object beam;
a beam combiner positioned to receive the reference beam and the object beam, combine the reference beam with the object beam to form a combined beam, and route the combined beam having a reference beam component and an object beam component directed along a common path via the transmit slot into a target medium, the target medium acting upon the combined beam to form a common path interference beam;
a polarizer configured to polarize the combined beam or the common path interference beam; and
an imaging sensor disposed downstream from the polarizer, the imaging sensor being configured to receive the common path interference beam via the receiver slot and generate common path interference beam data associated with the common path interference beam.

18. The apparatus of claim 17, wherein the transmit slot extends in a transmit direction and the receiver slot extends in a receive direction, the transmit direction and the receive direction intersecting at a measurement depth point within the target medium and defining a first angle between the transmit direction and the receive direction.

19. The apparatus of claim 18, further comprising a second imaging sensor;
wherein the mount further comprises a second receiver slot associated with the second imaging sensor;
wherein the second receiver slot extends in a second receive direction, the transmit direction and the second receive direction intersecting at a second measurement depth point within the target medium and defining a second angle between the transmit direction and the second receive direction; wherein the first angle is different from the second angle.

* * * * *